(12) United States Patent
Cink et al.

(10) Patent No.: US 8,124,129 B2
(45) Date of Patent: Feb. 28, 2012

(54) CRYSTALLINE FORM OF THE COMPOUND A-348441

(75) Inventors: Russell Drew Cink, Grayslake, IL (US); Daozhong Zou, Bridgewater, NJ (US); Marvin Robert Leanna, Grayslake, IL (US); Pascal H. Toma, Cary, NC (US); Michelle Andrée Long, Libertyville, IL (US)

(73) Assignee: Karo Bio AB, Huddinge (SE)

( * ) Notice: Subject to any disclaimer, the term of this patent is extended or adjusted under 35 U.S.C. 154(b) by 686 days.

(21) Appl. No.: 11/988,330

(22) PCT Filed: Jul. 12, 2006

(86) PCT No.: PCT/EP2006/006811
§ 371 (c)(1),
(2), (4) Date: Feb. 13, 2009

(87) PCT Pub. No.: WO2007/006561
PCT Pub. Date: Jan. 18, 2007

(65) Prior Publication Data
US 2009/0176754 A1    Jul. 9, 2009

(30) Foreign Application Priority Data
Jul. 12, 2005   (GB) .................................. 0514302.9

(51) Int. Cl.
A61K 9/14      (2006.01)
A61K 31/56     (2006.01)
(52) U.S. Cl. .......... 424/489; 514/179; 514/177; 514/178
(58) Field of Classification Search .................. 424/489; 514/179, 178, 177
See application file for complete search history.

(56) References Cited

FOREIGN PATENT DOCUMENTS
WO     2004/000869     12/2003

OTHER PUBLICATIONS von Geldern, et al., "Liver-Selective Glucocorticoid Antagonists: A Novel Treatment for Type 2 Diabetes," Journal of Medical Chemistry, 2004, vol. 47, pp. 4213-4230.

Primary Examiner — Shengjun Wang
(74) Attorney, Agent, or Firm — Todd E. Garabedian; Wiggin and Dana LLP

(57) ABSTRACT

There is provided a hemihydrate of $(3\beta,5\beta,7\alpha,12\alpha)$-7,12-dihydroxy-3-{2-[{4-[17β-hydroxy-3-oxo-17α-prop-1-ynylestra-4,9-dien-11β-yl]phenyl}(methyl)amino]ethoxy}cholan-24-oic acid in a crystalline form which is characterised by an X-ray diffraction pattern having major peaks at 2θ=6.58±0.2, 8.54+0.2, 12.28±0.2, and 19.68±0.2. This crystalline material is useful in the treatment of conditions associated with an excess of hepatic glucocorticoid response.

18 Claims, 6 Drawing Sheets

CRYSTALLINE FORM OF THE COMPOUND A-348441

CROSS-REFERENCE TO RELATED APPLICATIONS

This application is a U.S. National Stage application of International Application Ser. No. PCT/EP2006/006811 filed Jul. 12, 2006.

BACKGROUND OF THE INVENTION

This invention relates to an improved crystalline material and its use in the treatment of conditions associated with an excess of hepatic glucocorticoid response.

WO 2004/000869 relates to novel compounds which are liver selective glucocorticoid receptor antagonists. Example 1 describes the synthesis of (3β,5β,7α,12α)-7,12-dihydroxy-3-{2-[{4-[17β-hydroxy-3-oxo-17α-prop-1-ynylestra-4,9-dien-11β-yl]phenyl}(methyl)amino]ethoxy}cholan-24-oic acid (referred to in that example as (3β,5β,7α,12α)-7,12-dihydroxy-3-{2-[{4-[11β,17α)-17-hydroxy-3-oxo-17-prop-1-ynylestra-4,9-dien-11-yl]phenyl}(methyl)amino] ethoxy}cholan-24-oic acid). This compound is hereinafter referred to as Compound I, and has the formula:

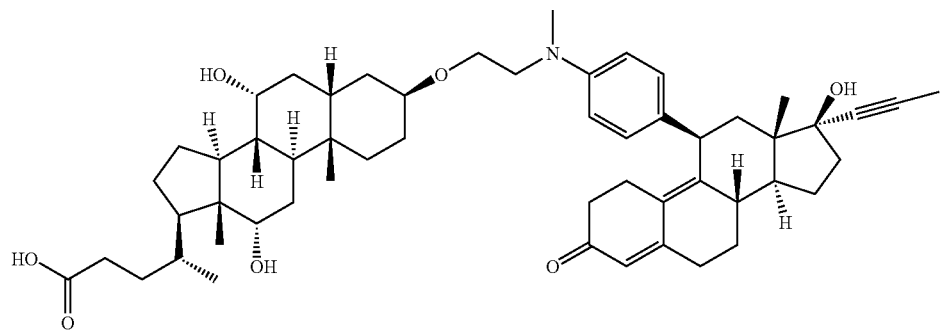

Unfortunately, synthesis of Compound I is rather difficult. The method of Example 1J of WO 2004/000869 leads to amorphous material, while the method of Example 1S leads to a crystalline form which is hygroscopic and not very stable.

BRIEF SUMMARY OF THE INVENTION

It has now been found that Compound I can be synthesised in the form of a hemihydrate having a novel crystalline form which has particular improved properties compared with the same compound in other forms.

Accordingly, the present invention provides the hemihydrate of (3β,5β,7α,12α)-7,12-dihydroxy-3-{2-[{4-[17β-hydroxy-3-oxo-17α-prop-1-ynylestra-4,9-dien-11β-yl]phenyl}(methyl)amino]ethoxy}cholan-24-oic acid (Compound I) in a crystalline form which is characterised by an X-ray diffraction pattern having major peaks at 2θ=6.58±0.2, 8.54±0.2, 12.28±0.2, and 19.68±0.2. Other significant but less prominent peaks may be found at 10.34±0.2, 15.10±0.2 and 15.46±0.2. A typical complete X-ray diffraction pattern is shown in FIG. 1. Table 1 gives those peaks having an intensity of greater than 20%.

TABLE 1

| 2-Theta | I % |
| --- | --- |
| 3.92 | 40.6 |
| 5.06 | 25.1 |
| 6.20 | 24.1 |
| 6.58 | 77.0 |
| 8.54 | 100.0 |
| 10.34 | 58.0 |
| 11.84 | 38.2 |
| 12.28 | 93.8 |
| 13.40 | 35.4 |
| 13.86 | 25.8 |
| 15.10 | 52.4 |
| 15.46 | 67.1 |
| 15.92 | 38.5 |
| 16.76 | 46.0 |
| 18.64 | 25.8 |
| 19.68 | 76.7 |
| 20.16 | 21.2 |
| 22.32 | 42.4 |
| 23.34 | 21.1 |
| 24.04 | 24.2 |
| 25.02 | 21.4 |

An additional way of characterising the novel crystalline material of the invention is by its differential scanning calorimetry (DSC) thermograms. Typically the material has a DSC thermogram which exhibits two endotherms, one with a maximum at 71±6° C. (and an extrapolated onset of 51±6° C.) and a more pronounced one with a maximum at 204±6° C. (and an extrapolated onset of 195±6° C.). Two typical DSC traces are shown in FIGS. 2 and 3.

Naturally, the exact details of any XRD or DSC pattern will depend upon a number of factors, for example the instrument used and the degree of purity of the material.

The novel crystalline material of the invention will be referred to as Form 1 throughout this Specification.

Preferably Form 1 is provided according to the invention at a level of purity in which at least 90%, especially at least 95%, most preferably substantially all, of the Compound I present, is Form 1.

Compound I can itself be synthesised as described in Example 1 of WO 2004/000869 or by methods described hereinafter. Resulting Compound I having a different physical structure from Form 1 may then be converted into Form 1 by a method which comprises dissolving the Compound I (not in Form 1) in a suitable solvent, for example nitromethane. Accordingly, the present invention also provides a method for the preparation of Form 1 of Compound I which comprises dissolving Compound I in a solvent comprising nitromethane, evaporating the solvent, and harvesting the resultant crystals of Form 1. Optimal yields are obtained when the nitromethane is evaporated slowly. Once crystals of Form 1 are obtained, further Form 1 can be obtained by preparing a solution of Compound I in a suitable solvent, seeding the resulting solution with crystals of Form 1, and then adding a further solvent to effect recrystallisation, the conditions being such that Form 1 is obtained following the seeding. Suitable solvents in this context include polar solvents, for example alcohols such as methanol, ethanol or isopropanol, or mixtures thereof, for example methanol/ethanol mixtures, and ketones, for example acetone, from which the Form 1 can be recrystallised by the addition of water.

In contrast to Form 1, another crystalline form, referred to as Form 2, and which is the anhydrate prepared in Example 1S of WO 2004/000869, has major X-ray diffraction peaks at 2θ=12.00±0.2, 13.60±0.2 and 15.34±0.2, with additional significant but lower intensity peaks at 6.28±0.2, 12.60±0.2, 14.90±0.2, 16.08±0.2, and 17.72±0.2. A typical complete X-ray diffraction pattern of Form 2 is shown in FIG. 3. Table 2 tabulates those peaks having an intensity of greater than 20%.

TABLE 2

| 2-Theta | I % |
| --- | --- |
| 6.28 | 61.2 |
| 8.34 | 25.0 |
| 10.12 | 22.4 |
| 11.22 | 26.0 |
| 12.00 | 100.0 |
| 12.60 | 68.0 |
| 13.60 | 91.4 |
| 14.90 | 86.0 |
| 15.34 | 99.5 |
| 16.08 | 62.1 |
| 16.72 | 30.1 |
| 17.20 | 45.5 |
| 17.72 | 54.7 |
| 18.92 | 46.1 |
| 20.86 | 45.4 |
| 22.10 | 33.0 |

Typically Form 2 has a DSC thermogram which exhibits a single exotherm with a maximum at 166±6° C. (and an extrapolated onset of 157±6° C.). A typical DSC trace of Form 2 is shown in FIG. 5. Amorphous compound I has a DSC thermogram which exhibits a single exotherm with a maximum at 157±6° C. (and an extrapolated onset of 149±6° C.). A typical DSC trace of amorphous Compound I is shown in FIG. 6.

Form 1 has been found to have a number of advantageous properties; in particular, it has a relatively high melting point and low solubility, thereby avoiding undesired precipitation in solution formulations. Importantly, it has improved stability and lower hygroscopicity compared with the known crystalline form of Example 1S of WO 2004/000869 and also with the amorphous form.

The invention also provides a pharmaceutical composition comprising Form 1 together with a pharmaceutically acceptable carrier. The pharmaceutical composition may for example be formulated for and administered to humans or other mammals orally, rectally, parenterally, intracisternally, intravaginally, intraperitoneally, topically (as by powders, ointments, or drops), bucally, or as an oral or nasal spray. It is preferably formulated for oral administration in solid or liquid form, for parenteral injection, or for rectal administration. Suitable forms of pharmaceutical composition, and methods of administration, include those described in WO 2004/000869.

Pharmaceutical compositions according to the invention may also contain one or more other therapeutic agents. Suitable compounds for use in combination therapy are listed in WO 2004/000869.

The crystalline material of the invention may be used for treating a condition associated with an excess of hepatic glucocorticoid response in a mammal, by antagonising the effects of the liver glucocorticoid receptors. Such conditions include diabetes (especially type II diabetes), hyperglycemia, hyperinsulinemia, inadequate glucose clearance, obesity, Syndrome X, hyperlipidemia, diabetic hypertension, or elevated hepatic glucocorticoid levels. It is especially useful in the treatment of diabetes, obesity or Syndrome X. Accordingly, the present invention also provides the crystalline material of the invention or a pharmaceutical composition containing it, for use in therapy; the use of such crystalline material or composition in the manufacture of a medicament for the treatment of a condition associated with an excess of hepatic glucocorticoid response in a mammal; and a method of selectively antagonizing the effects of the glucocorticoid receptors in a mammal which comprises administering a therapeutically effective amount of the crystalline material according to the invention or a pharmaceutical composition containing it, to the mammal.

The dosage level required in any individual case will depend upon various factors including the route of administration and the severity of the condition being treated. Generally dosage levels of about 0.1 to 50, more preferably of about 1 to about 10 mg of Compound I per kilogram of body weight per day are administered, preferably orally, to a patient. If desired, the effective daily dose may be divided into multiple doses for purposes of administration, e.g. two to four separate doses per day.

BRIEF DESCRIPTION OF DRAWINGS

The invention is illustrated by reference to the accompanying drawings, in which.

DETAILED DESCRIPTION OF THE INVENTION

Figure 1:
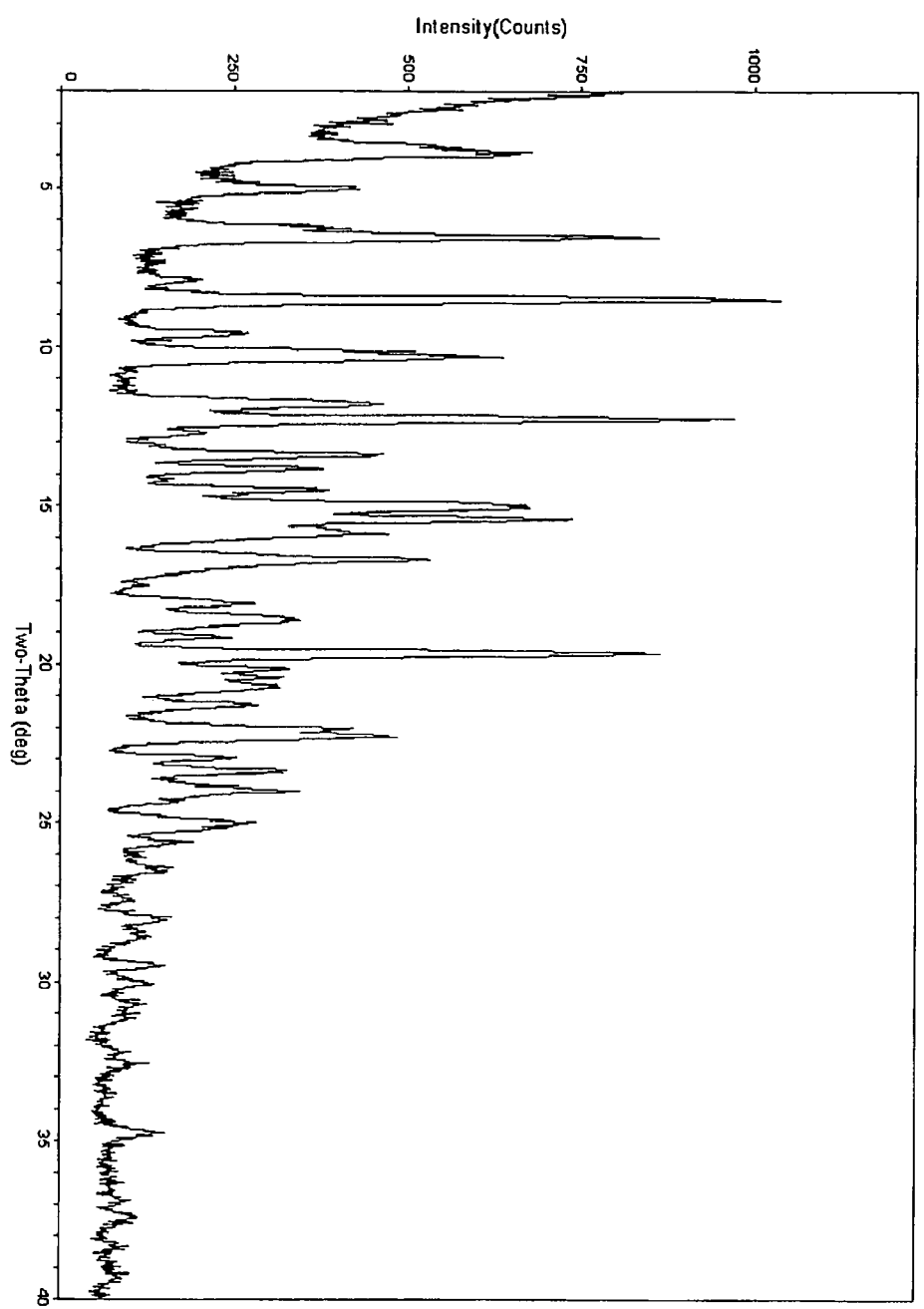
FIG. 1 is an XRD of Form 1.
Figure 2:
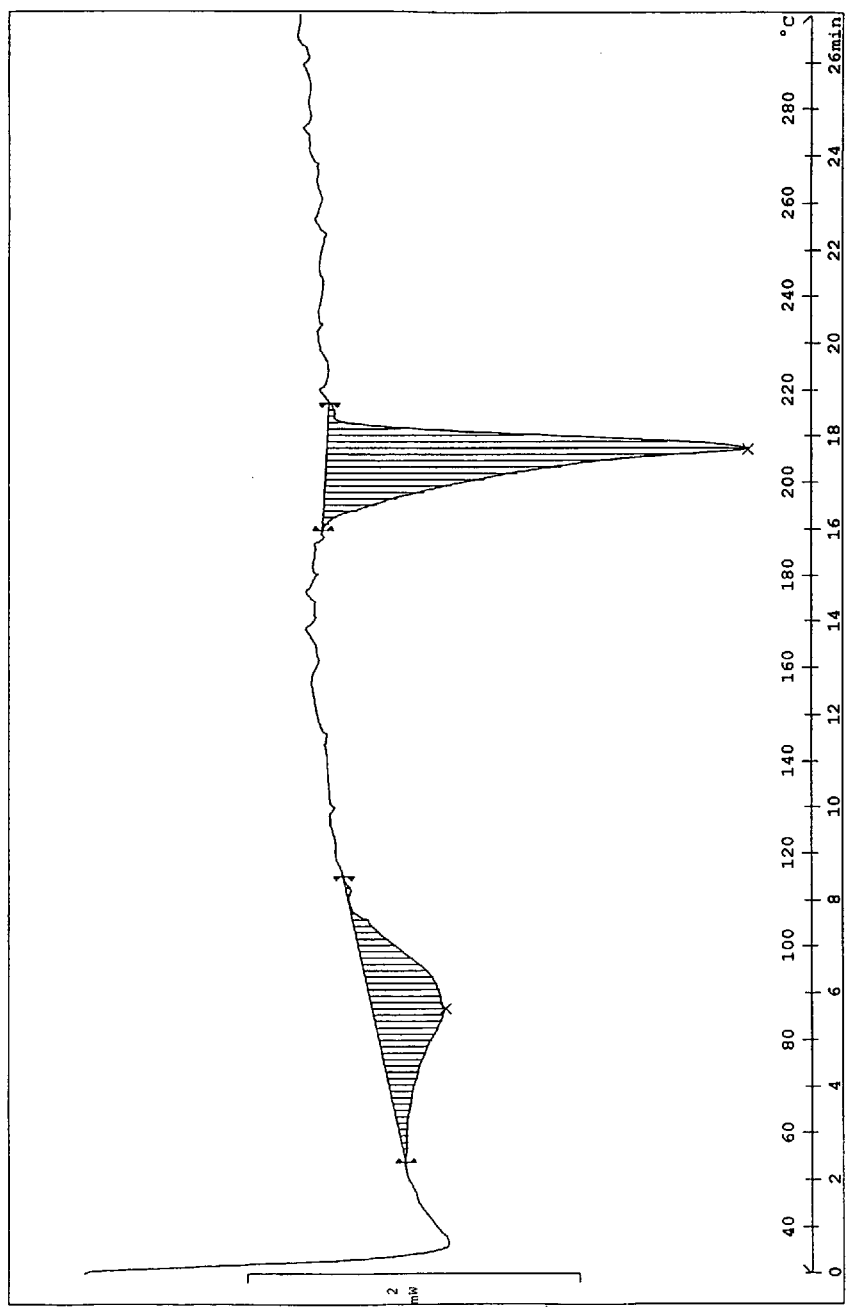
FIGS. 2 and 3 are differential scanning calorimetry traces of Form 1.
Figure 3:
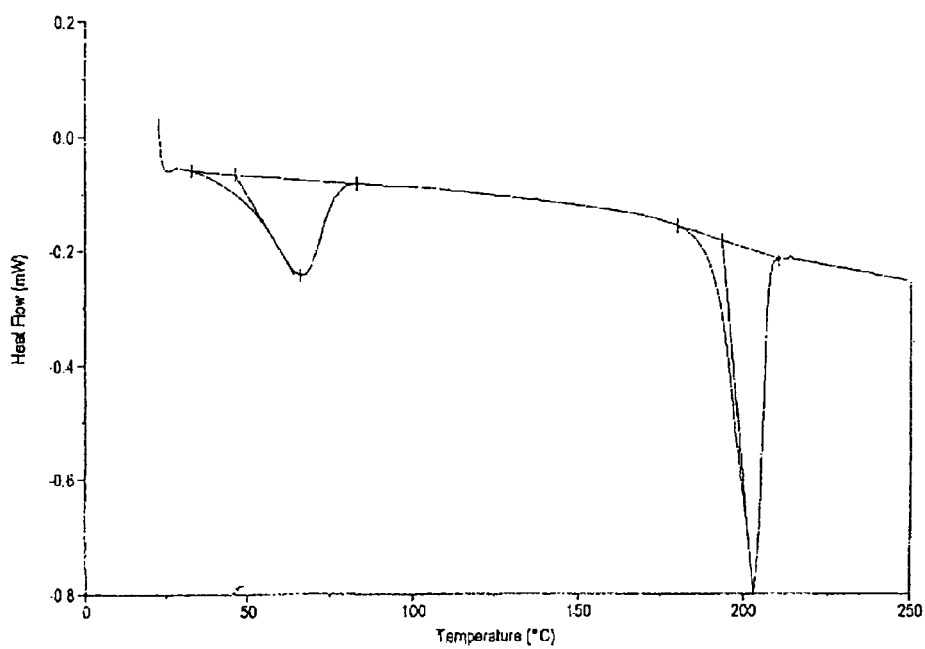
Figure 4:
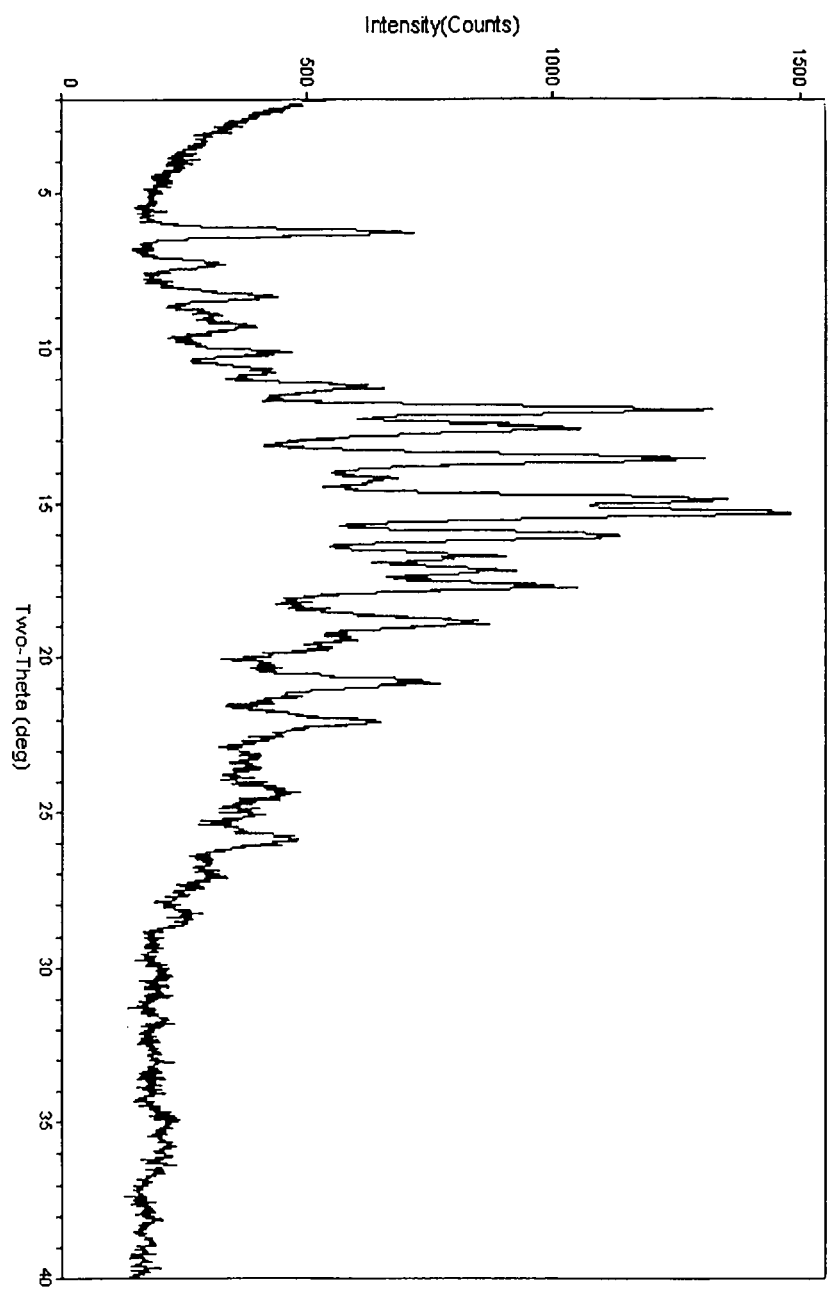
FIG. 4 is an XRD of Form 2.
Figure 5:
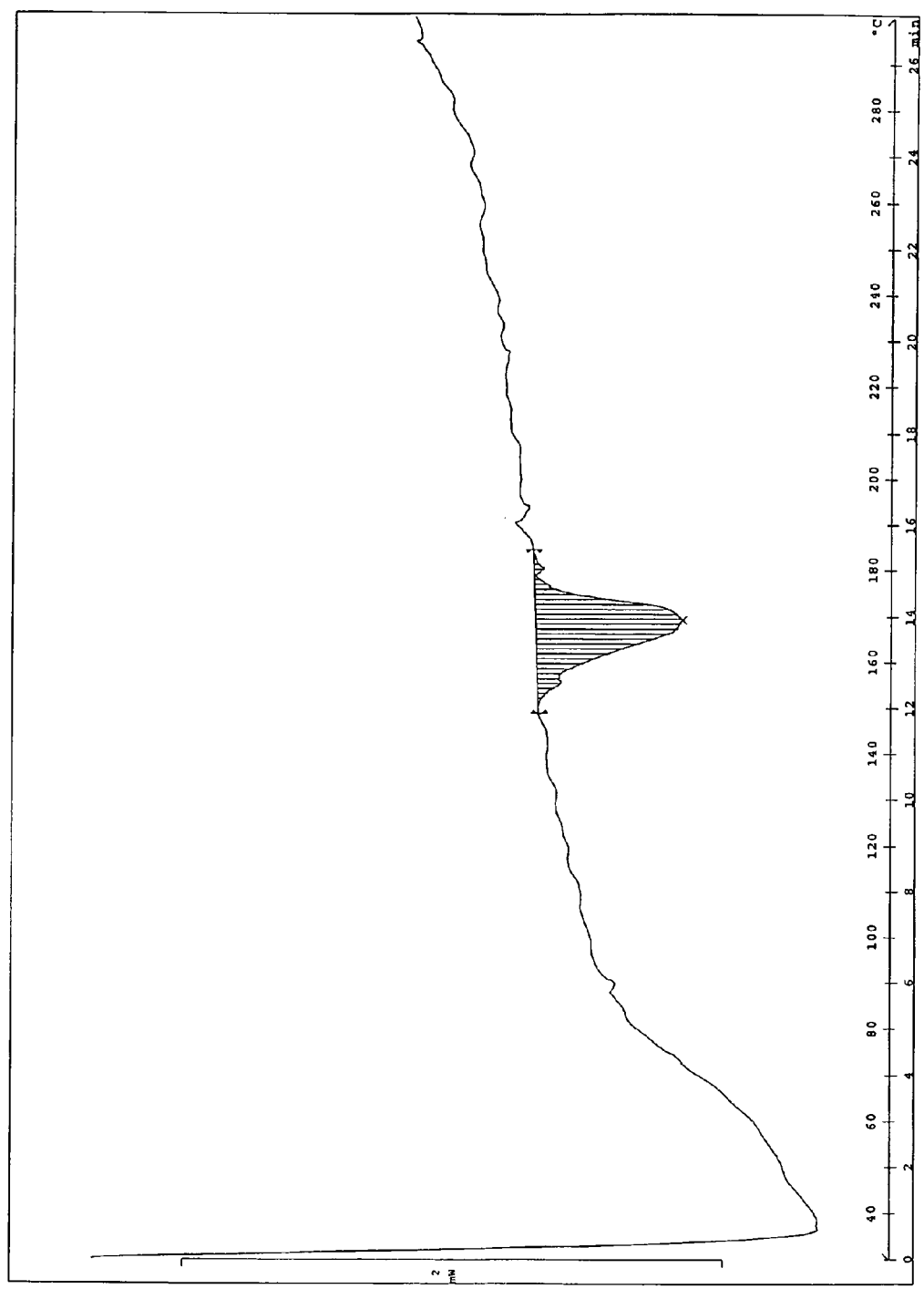
FIG. 5 is a differential scanning calorimetry trace of Form 2.
Figure 6:
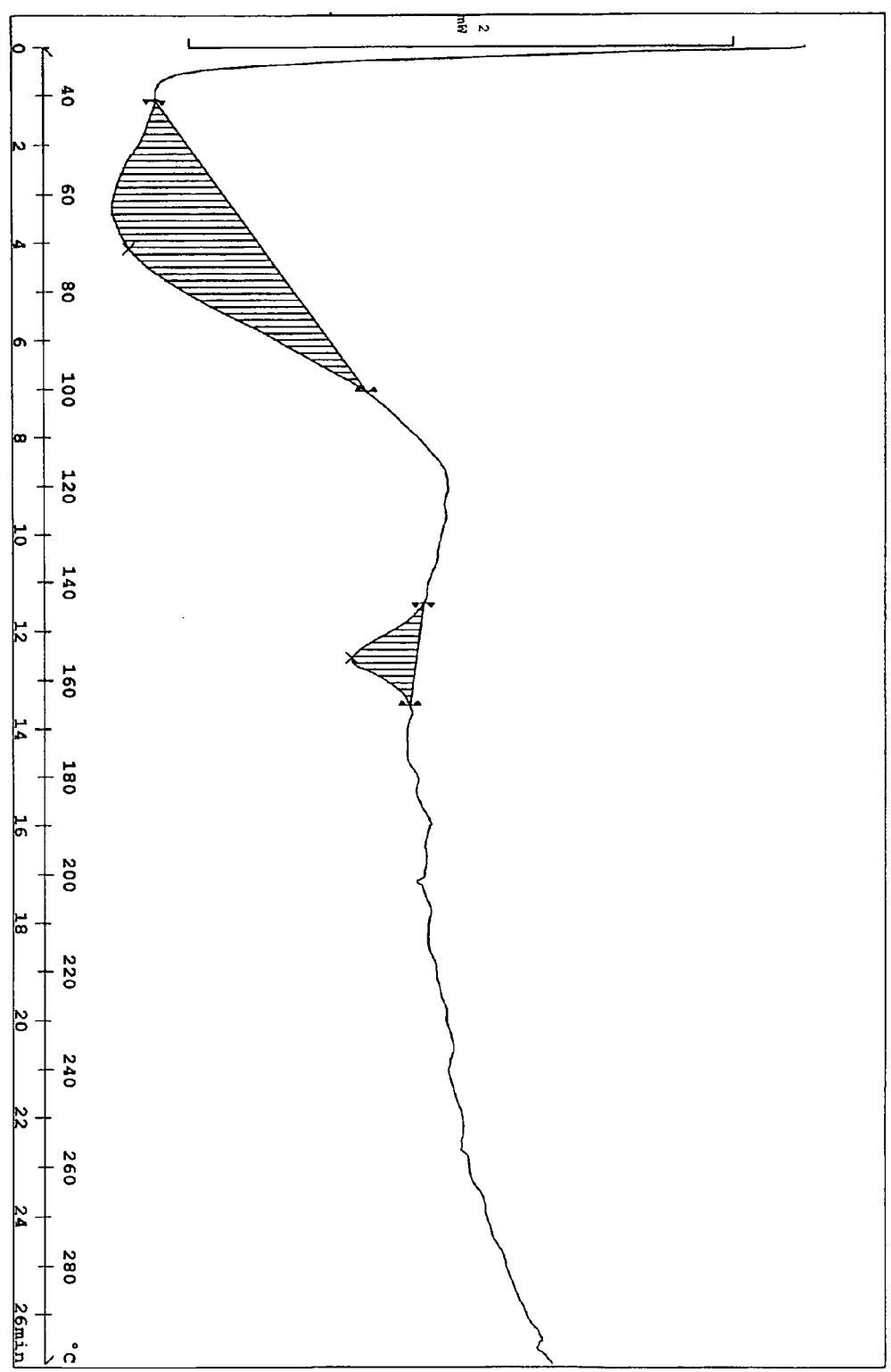
FIG. 6 is a differential scanning calorimetry trace of amorphous Compound I.

The following Examples illustrate the invention. X-ray powder diffraction was performed using an θ/θ diffractometer equipped with a 2 kW normal focus X-ray tube and a Peltier cooled germanium solid state detector with medium resolution Soller slits on both the X-ray tube and detector (model XDS 2000, Scintag Inc., Sunnyvale, Calif.). The source radiation was a copper filament X-ray tube operated at 40-45 kV and 30-40 mA. A corundum standard was analyzed to check instrument alignment. The instrument was computer-controlled using DMSNT software (Scintag Inc., Sunnyvale, Calif.). Analysis of data used MDI Jade 7 XRD Pattern Processing Software (ver. 7.0.8, Materials Data Inc., Livermore, Calif.). Typical XRDs of Forms 1 and 2 are shown in FIGS. 1 and 4, while typical DSC traces of Forms 1 and 2, and amorphous material, are shown in FIGS. 3, 5 and 6.

EXAMPLE 1 (COMPARATIVE)

Preparation of Compound I in Crystalline Form 2 and in Amorphous Form

A. Crystalline Form 2
A.1 Method 1

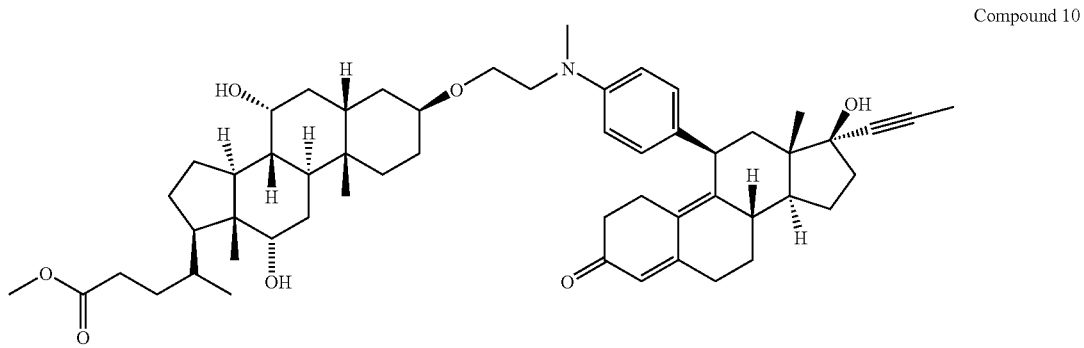

Compound 10

Compound 10 shown above, the methyl ester of Compound I, prepared as described in WO 2004/000869 (17.28 gms, 20.0 mmol, 91% chemical potency, therefore 15.72 grams, 18.2 mmol) was charged into a 500 mL three neck round bottom flask, equipped with an overhead mechanical stirrer, thermocouple and $N_2$ static bubbler. The reaction vessel was slowly vacuum purged with $N_2$ three times. The penultimate was then dissolved by addition of EtOH (173 mL). The solution was vacuum purged three times with $N_2$, and maintained under a static N2 bubbler throughout the course of the reaction. The resulting solution was cooled to +5° C. and treated with 3 N KOH (33.3 mL) at a rate to maintain an internal temperature <7° C. The reaction was allowed to stir at +5° C. until <0.6% remains of the sum of 10 and its ethyl ester analogue, as judged by HPLC. The reaction mixture was neutralized by 3N HCl (33.3 mL, 100 mmol) while maintaining the internal temperature <10° C. (end pH was adjusted from 4.63 to 4.87 with 0.2 mL of 3N KOH). The reaction mixture crystallized after a few minutes post addition of 3 N HCl. The reaction mixture was allowed to warm to ambient temperatures.

Polarized light microscopy showed plate-like crystals, which were shown by XRD to be Form 2.

A.2 Method 2

Compound 10 shown above (1.85 kg) was dissolved in ethanol (14.8 L) at 20° C. The solution was filtered through a cartridge filter and washed with ethanol (3.7 L). The solution was cooled to 5° C. and an aqueous solution of potassium hydroxide prepared by dissolution of potassium hydroxide (0.69 kg) in demineralised water (3.4 L) was added. The resulting mixture was stirred for 24 h at 5° C.

An aqueous solution of hydrochloric acid prepared by dilution of 33% aqueous hydrochloric acid (1.20 kg) with demineralised water (2.6 L) was added to adjust the pH to 4.7. The mixture was stirred for 30 min, the pH was checked, the mixture was heated to 20° C. and crystals of Compound I (2 g) were added. The suspension was heated to 40° C. and stirred for 3 h at this temperature. The suspension was cooled to 20° C. and stirred for 17 h. The product was filtered and washed with a mixture of demineralised water (1.2 L) and ethanol (1.2 L), with water (7×2.2 L) and with a mixture of demineralised water (0.6 L) and ethanol (0.6 L). The wet cake was dried at $T_{jacket}$=50° C. for 20 h. Yield of Form 2, was around 64% (1.17 kg).

B. Amorphous Form

Compound 10 shown above was dissolved in THF (5.2 g/g 10). The solution was cooled to 10° C. and treated with 1N LiOH (3 equiv.). The resulting slurry was allowed to warm to 25° C. over the course of 1 hour and stirred until less than 0.5% of 10 was observed by HPLC analysis (6 hours). The reaction mixture was diluted with MTBE (9.3 g/g 10) and neutralized with 1 M $H_3PO_4$ (1 equiv./equiv. LiOH). The mixture was poured into a separating funnel and the bottom aqueous layer was removed. The top organic layer was washed twice with 10% NaCl (12.2 g/g 10). The top organic layer was then extracted with 0.5N NaOH (5.23 g/g 10, then 0.6 g/g 10). The aqueous product containing layers were combined, diluted with water (17 g/g 10) and vacuum was applied, with stirring, to remove gross amounts of residual organic solvents until the weight of the mixture was approximately 26 g/g 10 (1 hour). The pH of the resulting thick suspension was adjusted to 5 by slow addition of 1.00M HCl, with vigorous stirring. The resulting gel-like solid was filtered through filter paper (Whatman 1) and washed twice with water (1.2 g/g 10). The product was transferred to drying trays and dried at 65° C. in a vacuum oven with an $N_2$ bleed until the water content was <5 wt % as measured on a Karl Fischer instrument (72 hours). The final product, amorphous Compound I, weighed 149.65 g at a potency of 100.6% for a potency-adjusted yield of 89%.

EXAMPLE 2

Preparation of Form 1

Into a 4 mL vial was placed 100 mg of amorphous Compound I and 1.0 mL of nitromethane was added. The vial was heated to 60 C for a minute and cooled to room temperature over about 5 minutes. The solids were filtered off and washed 4 times with 1 mL nitromethane. The filtrate was allowed to stand and slowly evaporate at ambient temperature over 7 days (lost approximately 2.5 mL (~2× concentrated). Fine needles were observed on the side of the flask. Some needles were scraped off and characterized as Form 1 by XRD and DSC.

EXAMPLE 3

Preparation of Form 1 by Seeding

Form 2 crystalline material prepared as in Example 1A above (1.14 kg) was added to ethanol denatured with isopropanol (5.7 L). The suspension was stirred at 20° C. and a small quantity of Form 1 (1 g) prepared as in Example 2 above was added. The suspension was stirred for 1 h, demineralised water was added over 1 h and the suspension was stirred for 2 h.

The yellow suspension turned to a creamy suspension. The product was filtered and washed with a mixture of demineralised water (1.0 L) and ethanol denatured with isopropanol (1.5 L). The wet cake was dried at $T_{jacket}$=50° C. for 63 h. Yield≈92.1% (1.05 kg). Form 1 was obtained in the form of a hemihydrate with a purity measured by HPLC of 98.1%.

EXAMPLE 4

Alternative Preparation of Form 1 by Seeding

Crystals of Compound I in Form 2 prepared as in Example 1A above (12.0 g) were slurried into ethanol (60 mL) in a 250 ml three neck round bottom flask equipped with a thermocouple, overhead mechanical stirrer assembly and an $N_2$ static bubbler. Crystals of Form 1 (10 mg) were added to the flask and stirred for 1 hour. Water (40 mL) was slowly added over 1 hour, and the flask was then stirred for 2 hours at ambient temperature. The resultant slurry was shown by polarized light microscopy and NMR to be fine crystals of Compound I in Form 1.

The slurry was filtered and washed 3 times with 60/40 ethanol/water (15 mL each time), and the resultant wet cake was dried for 10 days at 50° C. with an $N_2$ purge. The weight of isolated off-white crystalline solid was 10.92 g (91% recovery, 98.3% purity adjusted against a standard sample, with an assigned chemical potency of 100%.

EXAMPLE 5

Alternative Preparation Form 1 by seeding

A. Preparation of Form 1. Crystals of Compound I in Form 2 (3.00 kg) were added to ethanol denatured with isopropanol (15.0 L) and the mixture was heated to 78° C. until dissolution. The solution was cooled to 40° C. and the crystallisation was seeded with Form I (3 g). The suspension was cooled to 20° C. in 1 h and stirred at 20° C. for 1 h. Demineralised water (10.0 L) was added in 1 h and the suspension was stirred for 2 h. The product was centrifuged and washed with a mixture of demineralised water (2.6 L) and ethanol denatured with isopropanol (3.9 L). The wet cake was dried at $T_{jacket}$=50° C. for 16 h. Yield of Form 1: ≈87% (2.63 kg).

B. Recrystallisation of Form 1. Crystals of Form 1 prepared as described above (2.62 kg) were added to ethanol denatured with isopropanol (11.8 L) and the mixture was heated to 78° C. until dissolution. The solution was filtered on a cartridge filter and the filter was rinsed with ethanol denatured with isopropanol (1.3 L). The solution was cooled to 40° C. and the crystallisation was seeded with crystals of Form I (2 g). The suspension was cooled to 20° C. in 1 h and stirred at 20° C. for 1 h. Demineralised water (8.7 L) was added over 1 h and the suspension was stirred for 17 h. The product was centrifuged and washed with a mixture of demineralised water (2.3 L) and ethanol denatured with isopropanol (3.4 L). The wet cake was dried at $T_{jacket}$=50° C. for 24 h. Yield≈95% (2.48 kg).

EXAMPLE 6

Stability Study

Three samples of Compound I were packaged separately in double polyethylene bags in a small cardboard box, which were stored in a stability chamber under accelerated conditions (40° C./75% Residual Humidity). Sample 1 was 10 g of crystalline Form 1; Sample 2 was 2 g of amorphous product prepared as described in Example 1B above; and Sample 3 was 2 g of crystalline Form 2 made as described in Example 1A above.

Impurity profile, moisture content and crystalline form were measured on the samples, and then again approximately 3 months later for Sample 1, and 2 months later for Samples 2 and 3.

The impurity profile was measured by HPLC. The overall purity of Sample 1 did not change after 3 months, although the impurity profile was slightly modified. The overall purity of Sample 2 decreased slightly (96.7 instead of 97.3%). For Sample 3, this phenomenon was more marked, as the purity significantly decreased from 93.2 to 90.7%.

Karl Fischer analysis was used to measure moisture content. Sample 1 showed little water uptake, while Sample 2 showed significant increase (5% water, from an initially anhydrous product). Sample 3 showed an intermediate behaviour.

According to differential scanning calorimetry thermograms taken, Sample 1 showed no change in crystalline form over the test period of 3 months.

These experiments show that Compound I in Form 1 is more stable under accelerated conditions than Compound I in other forms.

We claim:

1. A hemihydrate of (3β,5β,7α,12α)-7,12-dihydroxy-3-{2-[{4-[17β-hydroxy-3-oxo-17α-prop-1-ynylestra-4,9-dien-11β-yl]phenyl}(methyl)amino]ethoxy}cholan-24-oic acid in a crystalline form which is characterised by an X-ray diffraction pattern having major peaks at 2θ=6.58±0.2, 8.54±0.2, 12.28±0.2, and 19.68±0.2.

2. A crystalline material as claimed in claim 1, characterised by an X-ray diffraction pattern additionally having significant peaks at 10.34±0.2, and 15.10±0.2 and 15.46±0.2.

3. A crystalline material as claimed in claim 2, characterised by an X-ray diffraction pattern containing major peaks as follows:

| 2-Theta | I % |
|---|---|
| 3.92 | 40.6 |
| 5.06 | 25.1 |
| 6.20 | 24.1 |
| 6.58 | 77.0 |
| 8.54 | 100.0 |
| 10.34 | 58.0 |
| 11.84 | 38.2 |
| 12.28 | 93.8 |
| 13.40 | 35.4 |
| 13.86 | 25.8 |
| 15.10 | 52.4 |
| 15.46 | 67.1 |
| 15.92 | 38.5 |
| 16.76 | 46.0 |
| 18.64 | 25.8 |
| 19.68 | 76.7 |
| 20.16 | 21.2 |
| 22.32 | 42.4 |
| 23.34 | 21.1 |
| 24.04 | 24.2 |
| 25.02 | 21.4. |

4. A crystalline material as claimed in claim 1, which has a differential scanning calorimetry trace which exhibits two endotherms, one with a maximum at 71±6° C. and one with a maximum at 204±6° C.

5. A crystalline material as claimed in claim 1, having a level of purity in which at least 90% of the (3β,5β,7α,12α)-7,12-dihydroxy-3-{2-[{4-[17β-hydroxy-3-oxo-17α-prop-1-ynylestra-4,9-dien-11β-yl]phenyl}(methyl)amino]ethoxy}cholan-24-oic acid present, is in the required crystalline form.

6. A crystalline material as claimed in claim 1 for use in a method of therapy.

7. A crystalline material as claimed in claim 6, for use in the treatment of diabetes, hyperglycemia, hyperinsulinemia, inadequate glucose clearance, obesity, Syndrome X, hyperlipidemia, diabetic hypertension, or elevated hepatic glucocorticoid levels.

8. A crystalline material as claimed in claim 7, for use in the treatment of diabetes, obesity or Syndrome X.

9. A crystalline material as claimed in claim 1, having a level of purity in which at least 95% of the (3β,5β,7α,12α)-7,12-dihydroxy-3-{2-[{4-[17β-hydroxy-3-oxo-17α-prop-1-ynylestra-4,9-dien-11β-yl]phenyl}(methyl)amino]ethoxy}cholan-24-oic acid present, is in the required crystalline form.

10. A crystalline material as claimed in claim 1, having a level of purity in which all of the (3β,5β,7α,12α)-7,12-dihydroxy-3-{2-[{4-[17β-hydroxy-3-oxo-17α-prop-1-ynylestra-4,9-dien-11β-yl]phenyl}(methyl)amino]ethoxy}cholan-24-oic acid present, is in the required crystalline form.

11. A method for the preparation of a crystalline material as claimed in claim 1, which comprises dissolving (3β,5β,7α,12α)-7,12-dihydroxy-3-{2-[{4-[17β-hydroxy-3-oxo-17α-prop-1-ynylestra-4,9-dien-11β-yl]phenyl}(methyl)amino]ethoxy}cholan-24-oic acid in a solvent comprising nitromethane, evaporating the solvent, and harvesting the resultant crystals.

12. A method for the preparation of a crystalline material as claimed in claim 1, which comprises preparing a solution of (3β,5β,7α,12α)-7,12-dihydroxy-3-{2-[{4-[17β-hydroxy-3-oxo-17α-prop-1-ynylestra-4,9-dien-11β-yl]phenyl}(methyl)amino]ethoxy}cholan-24-oic acid in a suitable solvent, seeding the resulting solution with a crystalline material as claimed in claim 1, and then adding a further solvent to effect recrystallisation, the conditions being such that the required crystalline material is obtained following the seeding.

13. A method as claimed in claim 12, in which the solvent is an alcohol or a ketone or a mixture of one or more alcohols and/or ketones, and the required crystalline material is recrystallised by the addition of water.

14. A pharmaceutical composition comprising a crystalline material as claimed in claim 1, together with a pharmaceutically acceptable carrier.

15. A method of selectively antagonizing the effects of the glucocorticoid receptors in a mammal which comprises administering a therapeutically effective amount of a crystalline material as claimed in claim 1 to the mammal.

16. A method of treating a mammal for diabetes, hyperglycemia, hyperinsulinemia, inadequate glucose clearance, obesity, Syndrome X, hyperlipidemia, diabetic hypertension, or elevated hepatic glucocorticoid levels which comprises administering a therapeutically effective amount of a crystalline material as claimed in claim 1 to the mammal.

17. A method of selectively antagonizing the effects of the glucocorticoid receptors in a mammal which comprises administering a therapeutically effective amount of a pharmaceutical composition as claimed in claim 14 to the mammal.

18. A method of treating a mammal for diabetes, hyperglycemia, hyperinsulinemia, inadequate glucose clearance, obesity, Syndrome X, hyperlipidemia, diabetic hypertension, or elevated hepatic glucocorticoid levels which comprises administering a therapeutically effective amount of a pharmaceutical composition as claimed in claim 14 to the mammal.

* * * * *